United States Patent [19]

Kolesar, Jr.

[11] Patent Number: 4,472,356

[45] Date of Patent: Sep. 18, 1984

[54] GAS CONTAMINATION DETECTION DEVICE

[75] Inventor: Edward S. Kolesar, Jr., Canton, Ohio

[73] Assignee: The United States of America as represented by the Secretary of the Air Force, Washington, D.C.

[21] Appl. No.: 343,136

[22] Filed: Jan. 27, 1982

[51] Int. Cl.³ ............................................. G01N 31/06
[52] U.S. Cl. ........................................ 422/88; 422/98
[58] Field of Search ................. 436/104, 151; 422/88, 422/98; 338/34; 324/71.5; 55/18, 19

[56] References Cited

U.S. PATENT DOCUMENTS

| | | | |
|---|---|---|---|
| 2,930,015 | 3/1960 | Blumer | 436/151 |
| 2,940,041 | 6/1960 | Jacobson | 324/71 |
| 3,831,432 | 8/1974 | Cox | 73/23 |
| 3,924,219 | 12/1975 | Braun | 338/34 |
| 3,999,122 | 12/1976 | Winstel et al. | 436/151 |
| 4,264,331 | 4/1981 | Klein et al. | 338/34 |

*Primary Examiner*—Hiram H. Bernstein
*Attorney, Agent, or Firm*—Donald J. Singer; William J. O'Brien

[57] ABSTRACT

A device for detecting the degree of contamination of a gas filter system by a contaminating gas. The device comprises a filter chamber having a pair of grids positioned therewithin and coated with a semiconductive polymer whole bulk conductivity changes due to a chemical reaction between the polymer and a contaminating gas. Measurement of the change is then utilized to indicate the degree of contamination in the filter system.

3 Claims, 5 Drawing Figures

GAS CONTAMINATION DETECTION DEVICE

STATEMENT OF GOVERNMENT INTEREST

The invention described herein may be manufactured and used by or for the Government for governmental purposes without the payment of any royalty thereon.

BACKGROUND OF THE INVENTION

This invention relates in general to a device for detecting and monitoring gas contaminated filter systems. More particularly, this invention concerns itself with a device which utilizes semiconducting polymers as a means for monitoring the degree of contamination of gas filters that are ultimately rendered useless as a gas filtering system due to the absorption of a contaminating gas on the filtering elements of the system. In a more specific aspect, the invention relates to a device for the continuous, real-time detection of chemical warfare agents, such as organophosphorous compounds, that are diffused through a charcoal filter and ultimately render it useless due to contamination.

The effect of pesticides and other chemical contaminants on the environment has generated considerable interest from an ecological standpoint. This interest has provided the impetus for a concentrated research effort in an attempt to develop monitoring systems for detecting the presence of contaminants in the environment. Because of the deadly and persistent effects produced by pesticides, and their structurally related chemical warfare counterparts, the development of simple, reliable and rugged detection systems, that are selective and sensitive to particular contaminants, has become a matter of vital importance to ecologically concerned groups as well as military strategists.

Many analytical methods have been developed for detecting chemical contaminants in water or soil. Gas chromatography, flame photometers and alkali-flame detectors are frequently employed. However, there are few methods and devices which monitor contaminants in the atmosphere.

With the present invention, however, there has been developed a device which meets the criteria of ruggedness, simplicity, reliability and sensitivity for detecting the organophosphorous compounds used as chemical warfare agents. The device is specifically useful in monitoring and detecting the degree of contamination which can occur in the charcoal filtering system used to filter out chemical warfare agents which may be contaminating a military environment such as the interior of trucks, tanks, aircraft, naval vessels and protective shelters.

The operating principle of this invention is based on measuring the bulk conductivity associated with semiconductive polymers that are specifically chemically reactive with organophosphorous chemical warfare compounds. The usefulness of the invention is found in the fact that a contaminant filtering unit replacement can be made based on the actual degree of contamination rather than on a somewhat haphazard and unreliable estimate of the potential operational life of the filtering unit.

SUMMARY OF THE INVENTION

The present invention concerns itself with a simple, rugged, reliable gas monitoring device that is selective and sensitive to the detection of organophosphorous chemical warfare compounds that are absorbed and diffused through a charcoal filter system and ultimately render the system useless due to contamination. The device uses a detecting system based on measuring the change of the bulk conductivity associated with semiconductive polymeric compounds. The polymers utilized by the invention are specifically chemically reactive with organophosphorous based chemical warfare agents.

In general, the device comprises a charcoal filtering system, a signal transducer and a reference transducer positioned within the charcoal filtering element in spaced relationship to one another, a log-ratio module interconnected to both transducers which in turn is connected to a voltage power source and a voltmeter. In operation, the device of this invention compares a first current flowing through the filter transducer to a second current flowing through the reference transducer, producing an output voltage proportionate to the ratio of the logarithm of the two currents. The proportionality between the two currents allows accurate measurement over a large range of input currents which will be determined by the amount of chemical contaminants that passes through the chemical filter element. Warning of excessive contamination of the filtering element can then be indicated by referring to the voltmeter which can be suitably marked to indicate "safe" or "replace" conditions for the filter element.

Accordingly, the primary object of this invention is to provide a monitoring or detecting device for determining the degree of contamination existing in a charcoal filtering element used to filter or decontaminate a gas contaminated environment.

Another object of this invention is to provide a device that is simple, rugged and effective in determining on a continuous and real-time basis the contamination of a charcoal filter by organophosphorous chemical warfare agents.

Still another object of this invention is to provide a device that is unique in its ability to specifically, effectively, and accurately detect organophosphorous compound contamination of a charcoal filter element by using semiconductive polymers.

A further object of this invention is to provide a detecting device that automatically compensates for substantial physical and environmental interference, such as temperature variations and filter air flow fluctuations by utilizing a semiconductor polymer coated reference transducer and an electronic bridge.

The above and still further objects and advantages of the present invention will become more readily apparent upon consideration of the following detailed disclosure thereof when taken in conjunction with the accompanying drawings.

DETAILED DESCRIPTION OF THE PREFERRED EMBODIMENT

Pursuant to the above defined objects, this invention concerns itself with a monitoring or detecting device used for determining the degree of contamination of a charcoal filtering element by a gaseous chemical contaminant such as an organophosphorous chemical warfare compound. The detector is utilized, in a specific manner, to monitor the degree of chemical warfare agent contamination, specifically organophosphorous nerve agents, associated with the large, expensive, charcoal filters used in collective protective shelters. "Safe" and "replace" warnings given by the detector alerts personnel to switch to an alternate filter pack or replace a contaminated one.

Figure 1:
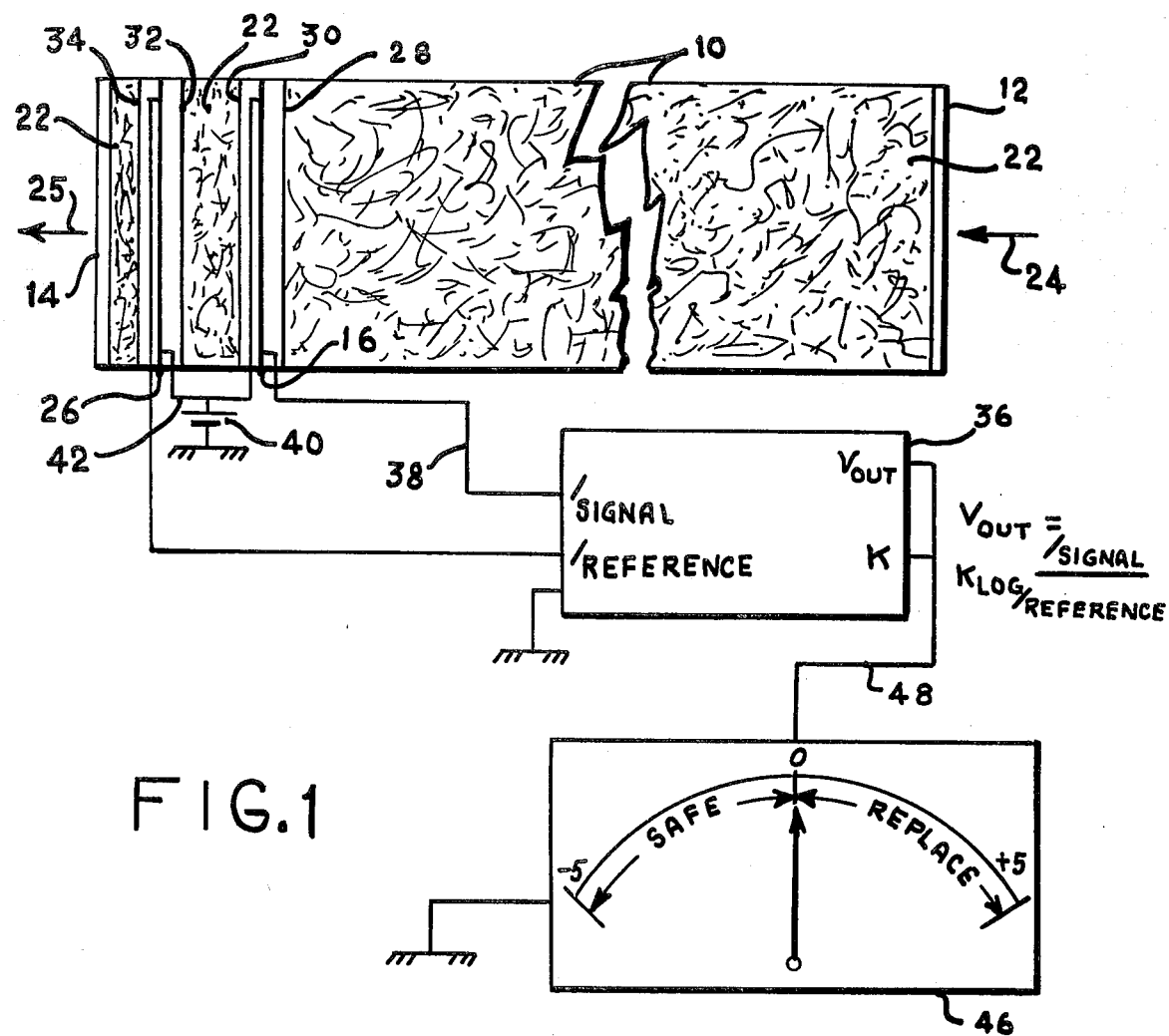
FIG. 1 is a schematic illustration showing the gas detecting device of this invention.
Figure 2:
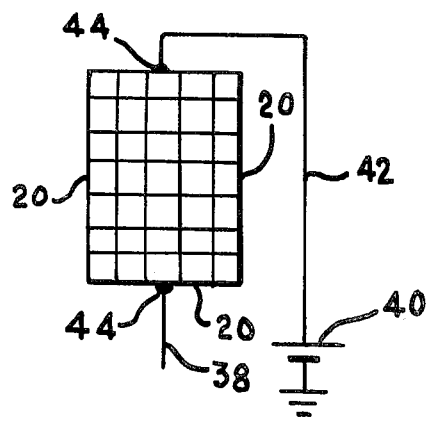
FIG. 2 is a side elevational view in simplified schematic form of a polymer coated nylon grid.
Figure 3:
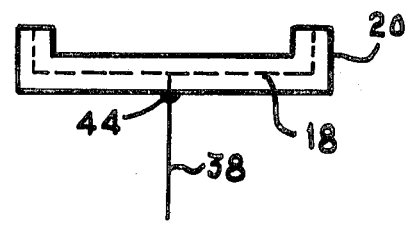
FIG. 3 is a bottom view, enlarged and in detail, of the polymer coated grid of FIG. 2.

With reference now to the drawings, wherein like reference numerals designate the same or similar elements in the various views, there is disclosed in FIG. 1 a detecting device which continuously detects the contamination of a filter by a gaseous contaminant. The device includes a chamber 10 having an inlet orifice 12 and an outlet orifice 14. A signal transducer 16, comprising a nylon grid 18 with a semiconductor polymer coating 20 as shown in greater detail in FIGS. 2 and 3, is positioned within a charcoal filtering medium 22 proximate to the outlet orifice 14 at an angle perpendicular to a flow of gas contaminated air 24 which passes into the filter medium 22 at inlet orifice 12. The contaminated air 24 is filtered as it passes through the chamber 10 and exits as clean air 25 at outlet orifice 14. A reference transducer 26, identical in design and construction to the signal transducer 16 is positioned downstream in spacial relationship and at a predetermined distance from the signal transducer 16. Paper filter elements 28 and 30, as well as 32 and 34, sandwich the transducer elements 16 and 26 respectively. The filter paper elements 28, 30, 32 and 34 act as an insulator between the charcoal filter medium 22 and the polymer coated transducers 16 and 26.

The polymer coating material 20 is characterized by having a predetermined bulk conductivity which changes due to a chemical reaction between the polymer material and the gas contaminant 24 flowing through the filter media 22. In addition to being of a semiconductive nature, the polymer is also selectively, chemically reactive and sensitive to the particular gas contaminant being filtered.

As shown in FIGS. 2 and 3, the polymer coating 20 may be deposited on the nylon grid 18 by any conventional coating technique, such as spraying, dipping or chemical vapor deposition. The nylon grid 18 acts as an insulator and is used to bind, support and expose a large surface area of the polymer to the potentially contaminated filter air flow 24. The filter paper elements 28, 30, 32 and 34 will readily diffuse organophosphorous contaminants but will prevent electrical conduction between the signal transducer 16 and the reference transducer 26.

The location of the signal transducer along the length of the charcoal filter is determined by the amount of warning time a user desires before a "replace" warning is given. The signal transducer 16 covers the entire filter cross-section to ensure detection of organophosphorous compounds, or other similar type contaminants, that might otherwise channel through unexpected paths. The chemical reaction of the organophosphorous gas contaminant with the polymer coating 20 on the signal transducer 16 will change the bulk conductivity (1/resistivity) of the polymer, and thus the current flowing through the transducer loop. The transducer loop includes a log-ratio module 36 which is connected to the signal transducer 16 and reference transducer 26 by conductor wire 38. A voltage source 40 is connected to the two transducers 16 and 26, by means of conducting wire 42. An epoxy adhesive 44 is utilized to attach the conducting wires 38 and 42 to the polymer coated grid 20. A conventional voltmeter 46 is connected by conducting wire 48 to the log-ratio module 36 with "safe" and "replace" warning indicators to warn of contamination. A flashing light or audible buzzer, when properly calibrated, could also be utilized to trip at specific output voltages to indicate contamination.

In order to compensate for such factors as temperature variations, air-flow perturbations, and the long-term chemical stability of the semiconducting polymer, the reference transducer 26 is utilized in the detector scheme. The reference transducer design is also illustrated in FIG. 2. This transducer is fabricated and otherwise identical to the signal transducer 18 except that it is mounted near the airflow outlet 14 of the charcoal filter 10. The relative position of the signal and reference transducers ensures that the signal transducer 16 will be contaminated first, but the reference transducer 26 will still be exposed to such variables as temperature and air-flow fluctuations. In addition the polymer 20 on the signal and reference transducers will age at the same rate.

In operation, the detector device of this invention compares the current flowing through the signal transducer 16 to that flowing through the reference transducer 26, producing an output voltage proportional to the ratio of the logarithm of these two currents as measured by the log-ratio module 36. This proportionality allows accurate measurements over a large range of input currents. The output voltage is equal to: k x log ($1_{signal}/1_{reference}$). For example, a constant reference current of $10^{-8}$ amperes, and signal currents ranging $10^{-3}$ to $10^{-8}$ amperes, yields outputs 0 to $+5$ volts for $k=1$ volt/decade. The inexpensive log-ratio module 36 is a standard electronic integrated circuit readily available from a number of manufactures (Analog Devices Corporation, Teledyne - Philbrick, Intronics, etc.).

For example the logarithmic ratio amplifier module, Model No. 757, manufactured by Analog Devices, Inc. has been found to be suitable for use with this invention.

The majority of polymer conductivity research has been associated with surface conductivity modifications. This invention, however, relies on the modification of the bulk conductivity of a polymer as a result of a specific chemical reaction. A number of examples of particular, semiconductive resins, or polymers found to be suitable for use with this invention are set forth in Table I as follows:

TABLE I

| Example No | Resin Polymers |
| --- | --- |
| 1. | Polyvinyl benzyl chloride (PVBC)-tetramethylethylene-diamine copper (II) chloride graft |
| 2. | Polyvinyl pyrolidone (PVP) + 2,2' bi-pyridine Copper (II) chloride |
| 3. | poly (copper phthalocyamine) |
| 4. | the polymeric square planar CU (II) complex of 15 diformyl-2,6-di-hydroxnaphthalene dioxime |
| 5. | poly (2- or 4-vinyl-N—methyl-pyridinium hydroxide doped with |

TABLE I-continued

| Example No | Resin Polymers |
|---|---|
| 6. | TCN di-μ- dihydroxo-bis-(N,N,N',N'—tetra-methylenediamine) dicopper (II) diperchlorate |
| 7. | As $F_5$ doped poly (paraphenylene sulfide) |

The resinous polymers outlined in Table I have been appropriately modified to exhibit a chemical reactivity with specific organophosphorous compounds. Suitable methods for preparing the polymers is set forth in the following examples:

EXAMPLE I

A. Preparation of Tetramethylethylenediamine, Copper (II) Chloride (TMEDA Chelate)—

3.41 grams (0.02 moles) of $CuCl_2.2H_2O$ was dissolved in 100 ml DMAC then 2.32 grams (0.02) tetramethylethylenediamine was added resulting in an azure precipitate. The precipitate was fitered, rinsed with 100 ml DMAC and dried in vacuo 65° for 12 hours (%Cu=63.5/286.5).

B. Preparation of Poly (Vinylbenzyl Chloride) System (PVBC solution)

—Approximately 25.0 grams vinylbenzyl chloride was placed in a 150 ml test to be equipped with an $N_2$ sparge and magnetic stirrer. 0.25 grams of AIBN was added to 75 ml of chloroform and the mixture was brought to 65° C., it was maintained at this temperature with constant stirring for 10 hours. The solution was cooled and the resulting polymer precipitated as feathery flakes by dripping slowly into hexane with high agitation. After drying at 60° C. in vacuo for 26 hours 18.9 grams of brittle, clear light green polymer was obtained. The polymer was redissolved in $CHCL_3$ to make a 10% (wt) solution with 0.656 meq $Cl^-$ per gram solution.

C. PVBC + Tetramethylethylenediamine-Copper (II) Chloride—10.0 grams of the 10% PVBC solution was added to 0.31 grams of the TMEDA CHELATE (63.5 grams Cu/286.5 grams chelate). The chelate partially dissolved. This solution was filtered and cast to form an emerald green film 7% by weight in copper.

EXAMPLE II

A. 2,2'-Bipyridine Copper (II) Chloride-Chelate—, 70 grams of $CuCl_2'2H_2O$ (0.01 moles) was dissolved in 60 ml DMAC then 1.56 grams (0.01 moles) 2,2'-Bipyridine was added resulting in a bright bluegreen precipitate after stirring for 5 minutes. The precipitate was filtered, washed with 100 ml of DMAC and dried in vacuo at 65° C. for 12 hours (% Cu=63.5/326.6).

B. PVP Solution—10.0 grams of PVP was dissolved in 90.0 grams $H_2O$ to form 10% (wt) solutions which gave clear hard films when cast. PVP films became sticky under humid conditions. To 10.0 grams of aqueous PVP solution 0.31 grams of TMEDA Cu (II) Chloride Chelate was added. This resulted in a dark blue film solution which was 7% Cu/PFP when cast as film.

C. PVP+2,2'-Bipyridine Copper (II) Chloride—10.0 grams of the aqueous PVP solution (10% wt) was added to 0.29 grams of the 2,2'-Bipyridine Copper (II) Chloride chelate. The resulting bluegreen solution contained much undissolved chelate. The chelate would not dissolve at all in DMAC but completely dissolved at 100° C. in the water solution to give a dark blue solution. Chelate reprecipitated on cooling and the solution turned bluegreen again. By adding 3.0 ml more $H_2O$, the solution cleared and was cast. Crystals were formed in the final film.

Prepared films from the polymers of Example 1 and 2 were placed in a suitable conductivity bridge and their resistance measured as a function of the concentration of HCl and Benzoyl Chloride (BZC).

HCl was selected in order to determine the affect of an ionizable, water soluble gas on the polymer systems. Benzoyl chloride was chosen as an analog of the fluorophosphate ester compounds because of its similar solubility, vapor pressure and reactive hydrolyzable acid halide functionality.

Chelate systems known to catalytically hydrolyze CW agents, such as organophosphorous compounds, were selected for testing and include 2,2'-Bipyridine Copper (II) Chloride and Tetramethylethylenediamine Copper (II) Chloride. The Chelates were dissolved in the hydrophilic polymer-polyvinylpyrolidone, and bound to or dissolved in the hydrophobic polymer-poly(vinyl benzyl chloride). The systems were formed into polymer films and placed in the resistance bridge and their resistance initially recorded. Response to pulse inputs of HCl at 1000 ppm magnitude and benzoyl chloride at ~25 ppm was also recorded under 100% humidity conditions.

The hydrophilic and hydrophobic polymer chelate systems were synthesized as summarized in Examples 1 and 2. The testing included a polyvinylpyrolidone (PVP) blank as well as 2,2'-Bipyridine. The PVBC systems included a poly(vinylbenzyl chloride) (PVBC) blank and the imbibed tetramethylethylenediamine Copper (II) chelate.

The HCl and benzoyl chloride tests were performed under 100% humidity conditions. After 100% humidity equilibration pulse inputs of HCl and benzoyl chloride under 1.0 liter per minute flow conditions were made by injection of the anhydrous gas and vapor into the test chamber. The volume and concentration of the sample were adjusted to give ~1000 ppm HCl and ~25 ppm benzoyl chloride concentrations at the maximum of the pulse response. The depression of resistance and reversibility were monitored.

The results of the HCl and benzoyl chloride response tests are tabulated in Table II. Single headed arrows, double headed arrows, and two arrows indicate irreversible, fully reversible and partially reversible pulse responses to the test injections.

The control poly(vinylbenzyl chloride) Polymer I of Table II demonstrated minor alterations in resistance on HCl or BZC exposure. The control hydrophilic polymer, poly(vinyl pyrolidone (III) polymer of Table II, however, was very responsive. This indicates the conductive potential of the water containing matrix associated with the hydroscopic PVP. It is realized that BZC will hydrolyze without a catalyst. It is postulated that the released HCl is responsible for the apparent reversible effect. The nonionic amide which results does not contribute to charge transfer.

The quaterized system, polymer II of Table II demonstrated the most dramatic results of the poly(vinylbenzyl chloride) based films.

TABLE II

Response of Semiconductive Polymer Systems to Hydrogen Chloride and Benzoyl Chloride

| Polymer System | Resistance Shift (OHMS) | |
|---|---|---|
| | HCl[a] | Benzoyl Chloride[b] |
| I. Poly(vinylbenzyl chloride) | $8.600 \rightarrow 8.475 \times 10^9$ | $8.200 \rightarrow 8.100 \times 10^9$ |
| II. PVBC-Triethylenetetramine-Graft Copolymer | $4.050 \rightleftarrows 1.500 \times 10^9$ | $4.112 \rightleftarrows 2.742 \times 10^9$ |
| III. PVBC-Triethylenetetramine-Copper (II) Chloride Graft Copolymer[c] | $4.650 \rightleftarrows 3.375 \times 10^9$ | $3.225 \rightleftarrows 2.475 \times 10^9$ |
| IV. PVBC-Tetramethylethylenediamine Copper (II) Chloride[c] Graft | $1.2 \times 10^{12} \rightleftarrows 1 \times 10^9$ | $1.155 \times 10^{12} \rightleftarrows 2 \times 10^9$ |
| V. Polyvinylpyrolidone (PVP) | $5.6 \times 10^9 \rightleftarrows 7.2 \times 10^7$ | $7.800 \rightleftarrows 5.100 \times 10^8$ |
| VI. PVP + Tetramethylenediamine Copper (II) Chloride[c] Graft | $1.350 \rightleftarrows 0.994 \times 10^7$ | $6.600 \rightleftarrows 5.600 \times 10^7$ |
| VII. PVP + Tetramethylethylenediamine Copper (II) Chloride + 2-Pyridine-Aldoxime Methiodide[c] | $4.800 \rightleftarrows 2.800 \times 10^7$ | $2.400 \rightarrow 1.100 \times 10^7$ |
| VIII. PVP + Triethylenetetramine Copper (II) Chloride[c] | $2.000 \rightleftarrows 0.330 \times 10^7$ | $1.300 \rightleftarrows 0.900 \times 10^7$ |
| IX. PVP + 2,2'-Bipyridine Copper (II) Chloride[c] | $3 \times 10^8 \rightleftarrows 6 \times 10^5$ | $3.000 \rightleftarrows 0.899 \times 10^8$ |

[a] ~1000 ppm pulse
[b] ~25 ppm pulse
[c] 7.0 percent Copper by weight of film
[d] 4.0 percent aldoxime by weight of film This system, while not very sensitive to atmospheric moisture, was extremely sensitive to ionizable species. Indeed, it was the only system of any tested, which exhibited a two order of magnitude change or greater with either species tested.

The PVP film imbibed with the same chelates, polymer IV of Table II, did not demonstrate this type response. Nor did a styrene imbibed system later tested with the same chelate.

BZC does not require high pH environments in order to hydrolyze although this will dramatically increase rate.

Figure 4:
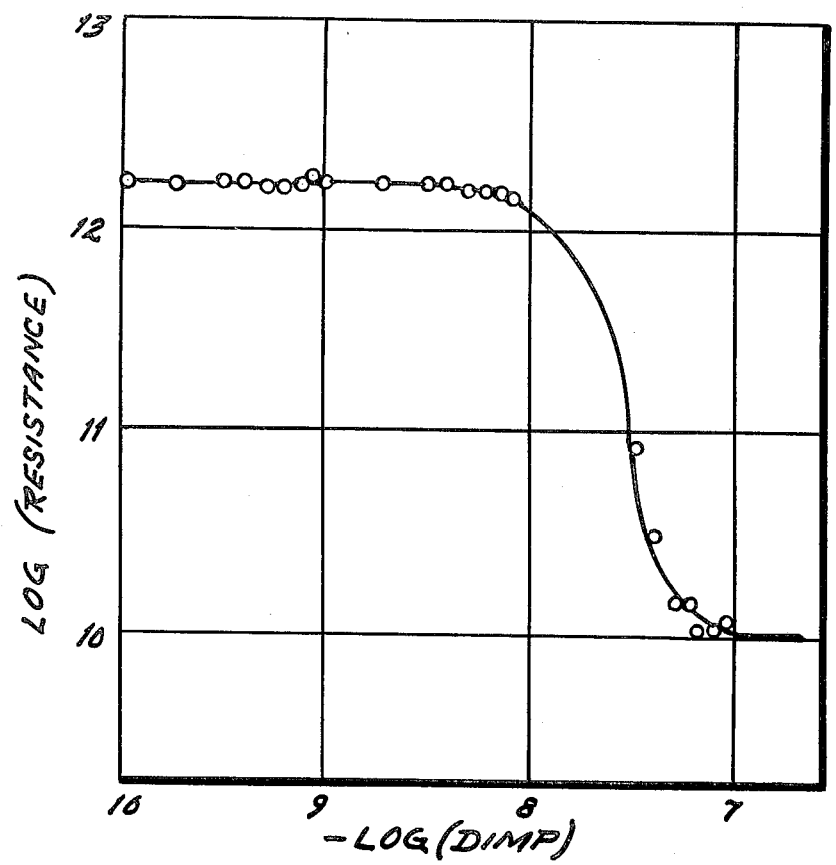
FIGS. 4 and 5 are graphs showing conductivity measurements.
Figure 5:
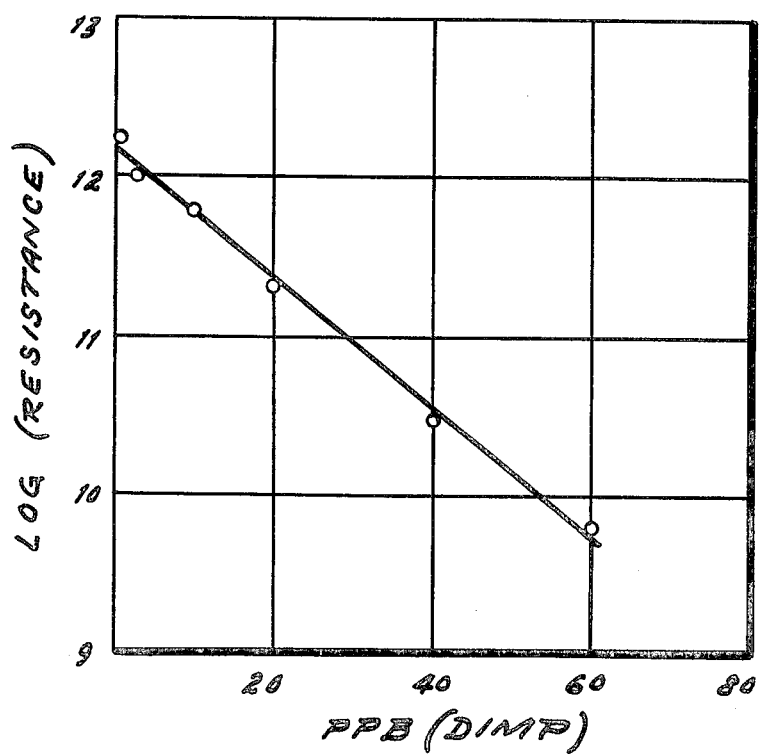

FIGS. 4 and 5 disclose semilogarithmic plots of conductivity response of polymers II and V, respectively of Table II, using diisopropyl methylphosphonate (DIMP) as an organophosphorous chemical warfare agent simulant in concentration ranges of from 0 to 60 parts per billion.

While particular embodiments of the present invention have been disclosed, it should be understood by those skilled in the art that various modifications and alterations can be made and that all such modifications as are embodied in the appended claims are intended to be included hereas.

What is claimed is:

1. A system for measuring the degree of contamination of a gas filter comprising:
   A. A filtering chamber forming an enclosure having an inlet positioned to accept the ingress and an outlet to provide egress of a flowing, contaminant containing gas;
   B. A filtering medium positioned within said filtering chamber for gas flow therethrough;
   C. A pair of means located proximate to said outlet in spaced relationship to one another across the path of the flow of said contamintant containing gas, each one of which comprises an insulator grid structure having a semiconductive polymeric material coated thereon and is capable of chemically reacting with the contaminant in said gas to produce a change in its electrical response which is dependent upon the amount of contaminant that has come in contact therewith;
   D. means for measuring the difference between the electrical response of each one of said last mentioned means; and
   E. indicating means responsive to said difference for indicting the degree of gas filter contamination.

2. A system in accordance with claim 1 wherein said polymeric material is characterized by having a predetermined bulk conductivity and is specifically and selectively chemically reactive to said contaminant in said flowing gas thereby effecting a change in the bulk conductivity after contact with said contaminant.

3. A system in accordance with claim 2 further including an electrical power source connected to each one of said pair of grid structures to effect in each a current flow therethrough to produce an output voltage; and means for indicating the proportionality of the ratio of the logarithm of the output currents.

* * * * *

UNITED STATES PATENT AND TRADEMARK OFFICE
CERTIFICATE OF CORRECTION

PATENT NO. : 4,472,356
DATED : September 18, 1984
INVENTOR(S) : Edward S. Kolesar It is certified that error appears in the above-identified patent and that said Letters Patent are hereby corrected as shown below:

On the title page:

Abstract line 5, "whole" should read --whose--.

Signed and Sealed this

Second Day of April 1985

[SEAL]

Attest:

DONALD J. QUIGG

Attesting Officer     Acting Commissioner of Patents and Trademarks